US00PP37116P2

(12) United States Plant Patent
Hansen

(10) Patent No.: US PP37,116 P2
(45) Date of Patent: Dec. 2, 2025

(54) ***BUDDLEIA* PLANT NAMED 'Cherry Royale'**

(50) Latin Name: *Buddleia davidii*
Varietal Denomination: Cherry Royale

(71) Applicant: Hans A. Hansen, Zeeland, MI (US)

(72) Inventor: Hans A. Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 18/831,463

(22) Filed: Jan. 29, 2025

(51) Int. Cl.
*A01H 5/02* (2018.01)
*A01H 6/00* (2018.01)

(52) U.S. Cl.
USPC ..... Plt./242
CPC ..... *A01H 6/00* (2018.05); *A01H 5/02* (2013.01)

(58) Field of Classification Search
USPC ..... Plt./242
CPC ..... A01H 5/02; A01H 5/00; A01H 6/00
See application file for complete search history.

(56) References Cited

PUBLICATIONS

Buddleja Diary 2024, retrieved on Apr. 2, 2025 at https://www.buddlejagarden.co.uk/bdiary/diary24.html#top, 33 pp. (Year: 2024).*
Facebook Walters Garden's Post 2024, retrieved on Apr. 2, 2025 at https://www.facebook.com/waltersgardens/posts/matt-pielin-one-of-our-regional-product-managers-is-pictured-next-to-cherry-roya/1260890331841739/, one page. (Year: 2024).*
Macore Variety Lister 2024-2025, retrieved on Apr. 2, 2025 at https://www.macore.com/files/2024-2025/2024-2025%20Macore%20Lister%20Herbaceous.pdf, 4 intro p. 112 (5 pp. total). (Year: 2025).*

* cited by examiner

*Primary Examiner* — June Hwu

(57) ABSTRACT

The new and distinct plant of *Buddleia* 'Cherry Royale' is a winter-hardy shrub with multi-stemmed, well-branched, rounded, mounded habit. The bright rose-pink, sweetly-fragrant flowers are held in many upwardly to slightly outwardly thyrse beginning in mid-summer and continuing until frost. Foliage is lanceolate and dark green above with silvery undersides. Fertility is reduced to nearly sterile. The new plant is valuable for landscaping en masse, as an accent or as a potted specimen.

2 Drawing Sheets

Botanical classification: *Buddleia davidii.*
Variety denomination: 'Cherry Royale'.

STATEMENT REGARDING PRIOR DISCLOSURES UNDER 37 CFR 1.77(B)(6)

The first offer for sale of *Buddleia* 'Cherty Royale' was Feb. 1, 2024, on a website listing with a brief description and photograph operated by Walters Gardens, Inc. *Buddleia* 'Cherry Royale' was later listed with a photograph and brief description in the "Walters Gardens 2024-2025 Catalog" initially distributed on May 23, 2024. Walters Gardens, Inc., obtained the new plant and all information relating thereto from the inventor. No plants of *Buddleia* 'Cherry Royale' have been sold in this country or anywhere in the world, nor has any disclosure of the new plant been made, more than one year prior to the filing date of this application, and such sale or disclosure within one year was either derived directly or indirectly from the inventor.

BACKGROUND OF THE PLANT

The present invention relates to the new and distinct butterfly bush plant of the Scrophulariaceae family, *Buddleia* 'Cherry Royale' hybridized by the inventor in the summer of 2018 at a wholesale perennial nursery in Zeeland, Michigan, USA. 'Cherry Royale' is the result of an ongoing breeding program conducted by the inventor. The goals for this program have been to produce improved, garden-worthy plants for the ornamental plant market. The new plant was the result of a single seedling selection from a cross between the unreleased proprietary hybrid 17-19-3 (not patented) as the female or seed parent and the male parent was an unreleased proprietary hybrid sibling with the in-house breeder code 17-17-x (not patented). The new plant was assigned the breeder code 18-15-4 to identify it during the evaluation trials.

*Buddleia* 'Cherry Royale' was first asexually propagated from a single select seedling in 2022 by stem cuttings at the same nursery in Zeeland, MI. The resultant asexually propagated plants have been found to be stable and true to type in successive generations of asexual reproduction.

SUMMARY OF THE INVENTION

Plants of 'Cherry Royale' have not been observed under all possible environmental conditions. The phenotype may vary somewhat with variations in environment and cultural practices such as temperature, light intensity, available moisture and fertility without, however, any variance in genotype.

In comparison to the new plant the female parent has lighter pink flowers, longer and wider inflorescences that cascaded downward. The male plant has longer thyrse that cascaded downward.

The nearest comparison plants known to the inventor are *Buddleia* 'Prince Charming' U.S. Plant Pat. No. 28,903, 'Pink Cascade' U.S. Plant Pat. No. 30,711, 'Pink Cascade II'

U.S. Plant Pat. No. 35,438, 'Pink Delight' (not patented), 'Pink Pagoda' U.S. Plant Pat. No. 23,214, and 'Queen of Hearts' U.S. Plant Pat. No. 27,987.

'Prince Charming' has a smaller habit and the flowers are bright cerise-pink on smaller thyrse. 'Pink Cascade' has flower thyrse are longer, more drooping, and a lighter medium-pink color. 'Pink Cascade II' has smaller habit and a larger drooping thyrse of a lighter pink color. 'Pink Delight' has a significantly larger habit with larger thyrse of lighter pink flowers. 'Pink Pagoda' is shorter and narrower in habit with more open and smaller thyrse having flowers of a lighter pink color with orange eyes. 'Queen of Hearts' has a much smaller habit and the flowers are a vibrant magenta-red.

*Buddleia* 'Cherry Royale' is a unique winter-hardy butterfly bush different from all other *Buddleia* cultivars known to the inventor based on the following combined repeatedly observed distinguishing traits:

1. Winter-hardy shrub with compact, multiple-stemmed, well-branched, rounded, mounded habit;
2. Many upwardly to outwardly thyrse flowering beginning mid-summer until frost;
3. Flowers with bright rose-pink petals;
4. Lanceolate foliage of dark green with silvery undersides;
5. Reduced fertility to nearly sterile.

BRIEF DESCRIPTION OF THE DRAWINGS

The photographs of the new plant demonstrate the overall appearance of the plant, including the unique traits. The colors are as accurate as reasonably possible with color reproductions. Ambient light spectrum, source and direction may cause the appearance of minor variation in color.

DETAILED BOTANICAL DESCRIPTION

Figure 1:
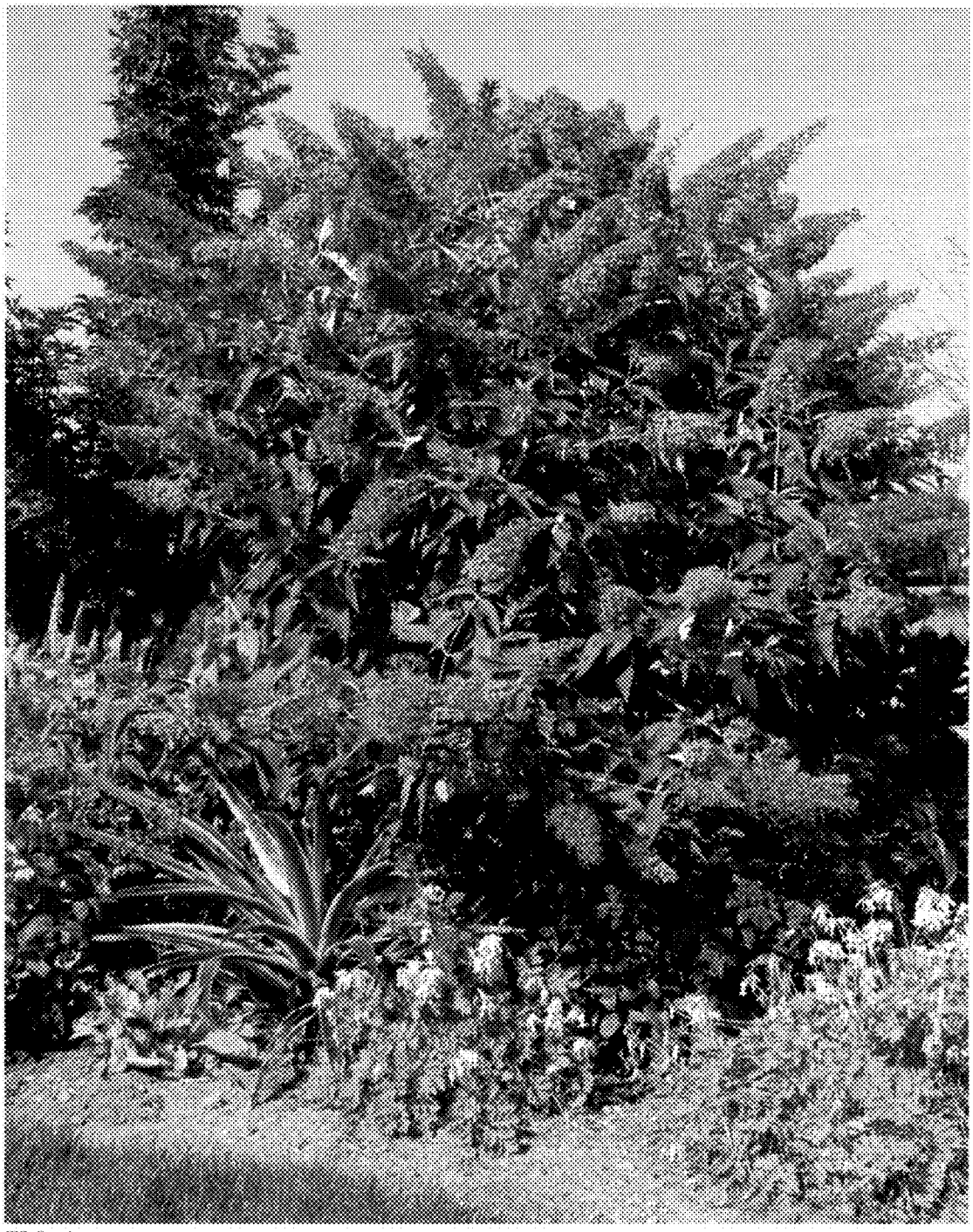
FIG. 1 shows the habit of a three-year-old plant in mid-season flowering.
Figure 2:
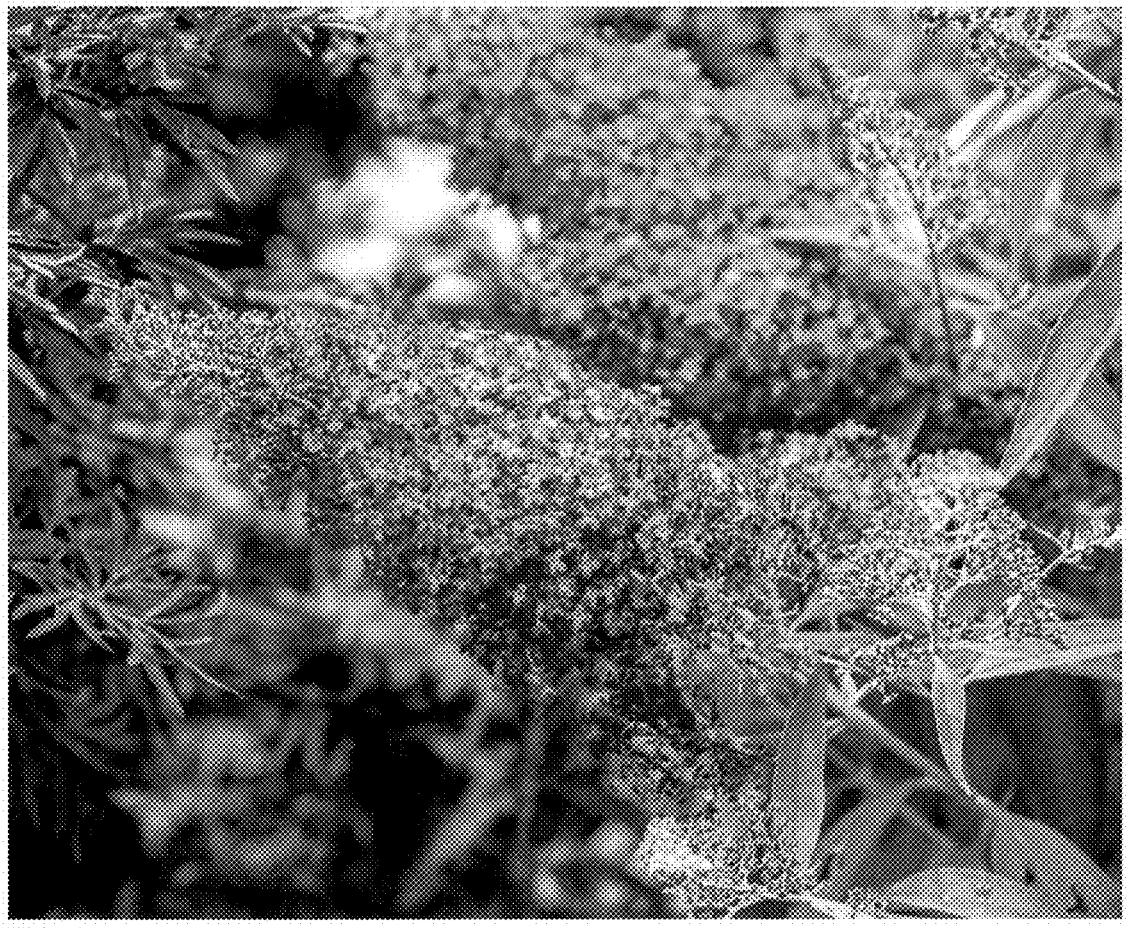
FIG. 2 shows a close-up of some inflorescences with flowers and buds.

The following descriptions and color references are based on the 2015 edition of The Royal Horticultural Society Colour Chart except where common dictionary terms are used. The new plant, *Buddleia* 'Cherry Royale', has not been observed under all possible environments. The phenotype may vary slightly with different environmental conditions, such as temperature, light, fertility, moisture, and maturity levels, but without any change in the genotype. The following observations and size descriptions are of a three-year-old plant in the loamy-sand, open-sun, field trials of a nursery in Zeeland, MI with supplemental fertilizer and water as needed. The plants are natural habit and were not treated with plant growth regulators, nor were they pinched at any time in the growth year except to cut back woody stems to about 15 cm tall in early spring.

Parentage: Unreleased proprietary hybrid 17-19-1 (not patented) as the female or seed patent; the male or pollen parent was an unreleased proprietary hybrid known as 17-17-x;

Propagation:

*Method.*—Softwood shoot cuttings.

*Time to initiate roots from tissue culture.*—About two weeks.

*Rooting habit.*—Normal, dense and branching, developing thick at base to about 1.5 cm diameter.

*Root color.*—Creamy white between RHS 159A and lighter than RHS 159D depending on soil type.

*Crop time.*—Under normal summer growing conditions 12 to 15 weeks to flower in a four-liter container from cutting. Plant vigor is very good.

Plant description:

*Plant shape and habit.*—Winter-hardy, herbaceous to semi-woody, well-branched shrub with about 7 thick upright and branched main stems producing a rounded mound, to about 180 cm tall and about 200 cm wide.

*Stem.*—Terete and woody in lower portion, with exfoliating bark; younger upper portion farinose; strong and flexible, arching or drooping especially in terminal thyrse; average about 160 cm tall from soil line to just below terminal flowers, and about 25 mm diameter at the base; about 18 branches per main stem before distal flowers in upper 9 nodes, extending at about 45° angle from main stem.

*Stem color.*—Young distal portion just below flowers between RHS 146C and RHS 195A with longitudinal ridges running downward from the outside the petiole and variably blushing of nearest RHS N186A; basal 30 cm between RHS N199C and RHS 165B with striations nearest RHS 199D.

*Nodes.*—To about 20 nodes per main stem below terminal thyrse, internode length on main stem average about 7 om on unpinched plant; upper internodes slightly more elongated than lower internodes.

*Node color.*—Distally between RHS 146C and RHS 195A and proximally between RHS N199C and RHS 165B with striations nearest RHS 199D.

Foliage description: Opposite; lanceolate; decussate; serrate with about four to six teeth per cm, teeth to about 1 mm long and 1 mm to 2 mm wide; glabrous adaxial, tomentulose abaxial; cuneate base and narrowly acute apex; no foliar fragrance detected;

*Leaf blade size.*—Up to about 180 mm long and about 60 mm wide, average about 115 mm long and about 40 mm wide; becoming smaller in distal portion of stem.

*Foliage color.*—Young expanding leaf adaxial distally nearest RHS 137A, proximally nearest RHS 157A, young expanding abaxial between RHS 195D and RHS 157A; mature Leaves adaxial between RHS 137B and RHS 137A, mature abaxial between RHS 194C and RHS 194B.

*Veins.*—Pinnate; adaxial glabrous, slightly impressed; abaxial costate, tomentulose.

*Vein color.*—Young adaxial midrib and primary veins nearest RHS 160D and secondary veins nearest RHS 137A, young abaxial midrib between RHS 145C and RHS 148C and primary and secondary veins nearest RHS 148D; mature adaxial midrib between RHS 161A and RHS 199D and primary and secondary veins between RHS 137B and RHS 137A, abaxial midrib between RHS 145A and RHS 146D and primary and secondary veins nearest RHS 148D.

*Petioles.*—Involute proximally, applanate distally; adaxial glabrous; abaxial farinose; to about 12 mm long and 3 mm wide at base.

*Petiole color.*—Adaxial nearest RHS 146D; abaxial between RHS 145A and RHS 146D; Inflorescence description: glomerate thyrse consisting of about 2,000 to 3,500 self-cleaning salverform flowers; terminal thyrse to about 36 cm long and 19 cm wide at base; average about 30 cm long and 10 cm wide; beginning in mid-July and continuing until frost in Michigan; thyrse effective for about three weeks; flower compactness very dense.

*Inflorescence aspect*.—Outwardly.

*Flower buds one day prior to opening*.—Elongated clavate; apex rounded; glabrous; about 13 mm long, club portion about 2.5 mm diameter, tube about 1 mm diameter and about 10 mm long.

*Flower bud color*.—Between RHS 72A and RHS 71A in club portion, exposed corolla tube between RHS 63B and RHS 63C; calyx nearest RHS 137A with margins nearest RHS 187B.

*Calyx*.—Campanulate; to about 3 mm to 4 mm long and 1 mm wide at apex.

*Sepals*.—Typically, four; adpressed to corolla tube; acute apex; glabrous adaxial and abaxial; margin entire; fused in about the basal 2 mm; individually about 0.7 mm wide at fusion.

*Sepal color*.—Nearest RHS 148C with moderate to solid RHS 187A in high light exposure.

*Flowers*.—Salverform; actinomorphic; perfect; to about 12 mm long and an abruptly applanate face 10 mm wide; with straight terete corolla tube about 10 mm long, and 2 mm diameter near face, and 1 mm diameter at base; aspect outward from thyrse center; remaining on the thyrse and effective for about five to seven days.

*Flowers fragrance*.—Pleasantly and distinctly sweet.

*Petals*.—Typically, four, rarely five; glabrous adaxial and abaxial blades and abaxial tube, puberulent center abaxial tube; blade rotund to obovate with crenate margin; apex rounded; blade to about 4 mm across and about 5 mm long from throat to apex.

*Petal color*.—Variable; upon initial opening adaxial blade nearest RHS 71C, when mature between RHS N66C and RHS N66D; initial abaxial blade nearest RHS 71B with no significant change in abaxial lobe color with maturity.

*Corolla tube color*.—Distal portion of adaxial corolla tube or throat nearest RHS 23A, distal portion of abaxial corolla tube nearest RHS 42C; proximal 1 mm of adaxial and abaxial corolla tube nearest RHS N155D; with no significant change in corolla tube color with maturity.

*Corolla blade attitude*.—At full bloom erect, outwardly, and downwardly depending on position on thyrse.

*Corolla lobe arrangement*.—Free; overlapping only minimally at base.

*Gynoecium*.—Pistil: one; about 4 mm long. Style: glabrous; glutinous; cylindrical; about 1.5 mm long and about 0.3 mm diameter; color nearest RHS 145D; Stigma: narrow ellipsoidal, lustrous; about 1 mm long and about 0.3 mm in diameter; color nearest RHS 145A; Ovary: superior; ellipsoidal; rounded base and rounded apex; about 1.5 mm tall and 1 mm across at base; color nearest RHS 144A.

*Androecium*.—Four; vestigial. Filaments: about 0.2 mm long and less than 0.1 mm diameter; adnate to the middle of adaxial corolla tube about 5 mm from base; color nearest RHS NN155D; Anthers: typically, four; ellipsoidal; basifixed; about 1 mm long and 0.3 mm wide; color nearest RHS 158A; Pollen: not observed.

*Pedicel*.—Short; cylindrical; farinose; about 2 mm long and about 0.5 mm diameter.

*Pedicel color*.—Nearest RHS 148C with moderate to solid RHS 187A in high light exposure.

*Peduncle*.—Quadrangular; farinose, flexible and strong; to about 42 cm long, and about 5 mm across at base below flowers;

*Peduncle color*.—Between RHS 146C and RHS 195A, proximal portion also with longitudinal ridges running downward from the outside the petiole and variably blushing of nearest RHS N186A.

Fruit: Rare to nearly sterile despite growing in trials with large number of pollinators where seed set on other *Buddleia* is common; when present, oblong cylindrical; 4-valved dehiscent capsule; to about 7 mm long and 1.5 mm diameter; acute apex; color nearest RHS 166B;

Seed: Rare; elongated ellipse with sharply acute apex and base; to about 3 mm long and about 0.1 mm diameter in center.

Seed color: Center 0.7 mm RHS 200C; apex and base between RHS N199D and RHS N199C.

Disease resistance: Typical resistance has been noted to deer browsing; other pest and disease resistance beyond that common to butterfly bush cultivars has not been observed.

Growth: The plant grows best with plenty of moisture and adequate drainage but it is able to tolerate some drought when mature.

Hardiness at least from USDA zone 5 through 10 with some occasional stem dieback in cold winters.

It is claimed:

1. A new cultivar of winter-hardy butterfly bush, *Buddleia* plant named 'Cherry Royale' as herein illustrated and described.

* * * * *